(12) United States Patent
Huang et al.

(10) Patent No.: US 7,107,094 B2
(45) Date of Patent: Sep. 12, 2006

(54) ANALYSIS METHOD ABOUT RELATIONSHIP OF BEATING SIGNAL AND HEART FUNCTION

(75) Inventors: Liang-Hsiung Huang, Taipei (TW); Shih-Fang Huang, Pingtung (TW)

(73) Assignee: Ostar Meditech Corp., Taipei Hsien (TW)

( * ) Notice: Subject to any disclaimer, the term of this patent is extended or adjusted under 35 U.S.C. 154(b) by 270 days.

(21) Appl. No.: 10/747,282

(22) Filed: Dec. 30, 2003

(65) Prior Publication Data
US 2005/0148888 A1 Jul. 7, 2005

(51) Int. Cl.
*A61B 5/0402* (2006.01)
(52) U.S. Cl. ..................... 600/509; 600/513
(58) Field of Classification Search ........ 600/481–485, 600/508, 509, 513, 514
See application file for complete search history.

(56) References Cited

U.S. PATENT DOCUMENTS 6,050,951 A * 4/2000 Friedman et al. ........... 600/485

* cited by examiner

*Primary Examiner*—Scott M. Getzow
(74) *Attorney, Agent, or Firm*—Rosenberg, Klein & Lee

(57) ABSTRACT

This is one analysis method about probing into relationship of beating signal and heart function. It is used to deal with one beating signal, which is measured from one subject under any activity condition in a period of time with an electric manometer. And this analysis could be the reference target of the heart function of the subject. This method includes: (1) to transform the beating signal into the power spectrum, (2) to normalize the outcome of the power spectrum transformation, and (3) to compute an advance defining heart index from the normalized power spectrum diagram, and supply the reference target of the heart function from the subject with the heart index.

19 Claims, 9 Drawing Sheets

ANALYSIS METHOD ABOUT RELATIONSHIP OF BEATING SIGNAL AND HEART FUNCTION

BACKGROUND OF INVENTION

1. Field of the Invention

The invention relates to an analysis method, and more particularly, to an analysis method that utilizing the beating signal measured under any activity condition with an electric manometer to be a reference target for determining the relationship of the beating signal and the heart function.

2. Description of the Prior Art

The heart disease is always called "the invisible killer", and when a patient is found having the heart disease, it is generally the last phase and cannot be cured. In fact, for the worldwide medical treatment, the initial and medium phases of the heart disease are hard to be found, and this causes many cases of dying in heart strike.

In comparison with the prophylaxis of the heart disease, the manometer has become popular in every family with its cheap price, and the prophylaxis of the high blood pressure can be easily carried out. The electric manometer is the most popular one for families or individuals with its simple operation. The electric manometer not only can measure the systolic pressure and the diastolic pressure but also can measure the pulse signal, such as the pulse count, for user reference. However, the pulse signal is one auxiliary function of the electric manometer, and is not paid much attention.

SUMMARY OF INVENTION

It is therefore a primary objective of the claimed invention to provide an analysis method utilizing the beating signal measured with the electric manometer to be a reference target for determining the relationship of the beating signal and the heart function.

It is therefore another objective of the claimed invention to provide an analysis method about probing into relationship of a beating signal and a heart function that is suitable to a subject under any activity condition.

The present invention discloses an analysis method about probing into relationship of a beating signal and a heart function. The method can be used to deal with the beating signal measured from a subject under any activity condition in a period of time with an electric manometer, and the analysis can be reference target of the heart function of the subject. The method comprises: (1) transforming the beating signal into a power spectrum by performing a power spectrum transformation; (2) normalizing the power spectrum outputted by the power spectrum transformation; and (3) computing a pre-defined heart index from the normalized power spectrum, and supplying the reference target of the heart function from the subject with the heart index.

The present invention further discloses a method for determining a heart function with a beating signal. The method comprises: (1) transforming the beating signal of a subject into a power spectrum by performing a power spectrum transformation; (2) normalizing the power spectrum outputted by the power spectrum transformation; (3) computing a pre-defined heart index from the normalized power spectrum; and (4) determining the heart function of the subject according to the heart index.

These and other objectives of the present invention will no doubt become obvious to those of ordinary skill in the art after reading the following detailed description of the preferred embodiment that is illustrated in the various figures and drawings.

Figure 1:
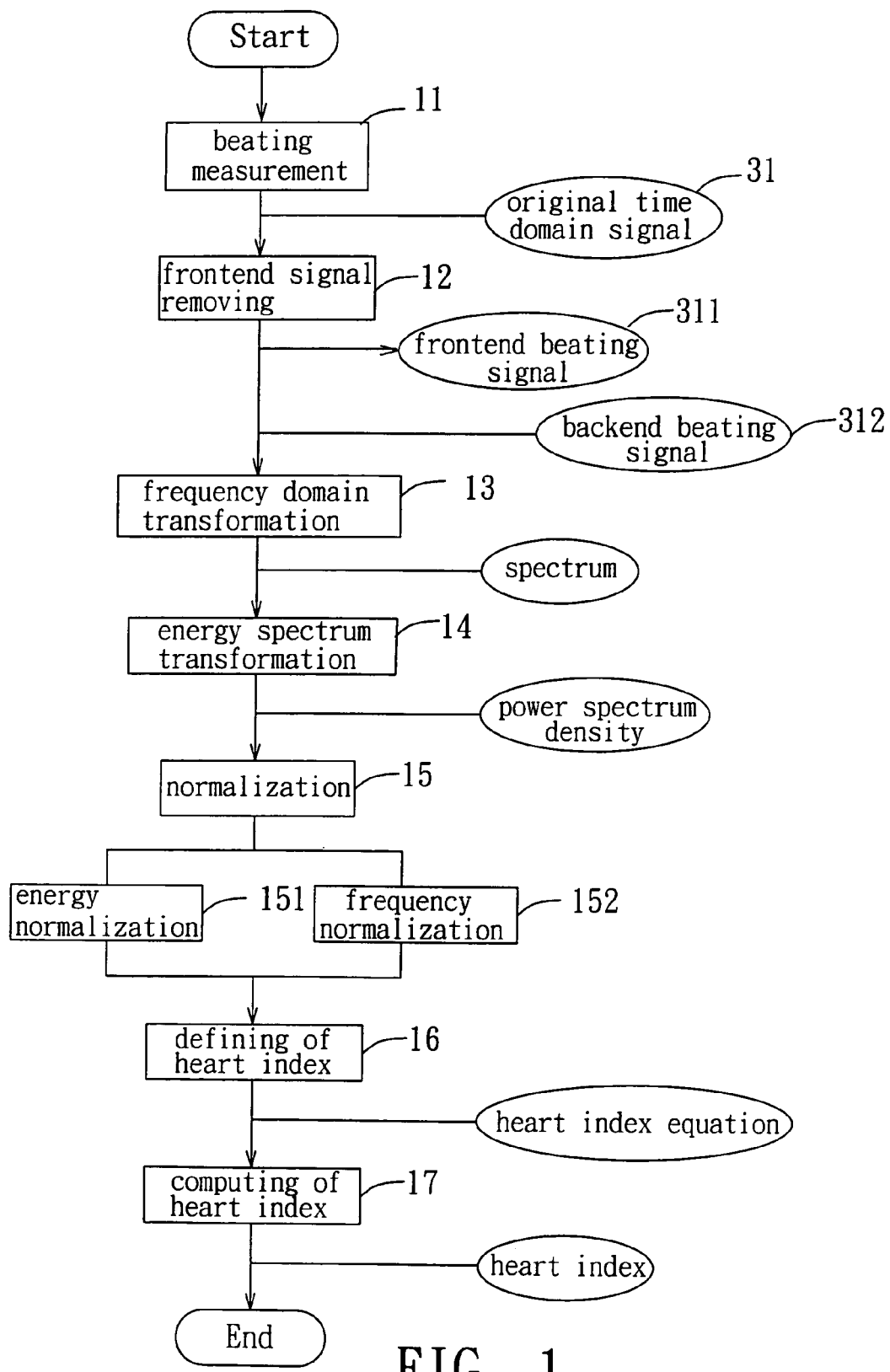
FIG. 1 is a flow chart of a preferred embodiment of an analysis method for determining the relationship of the beating signal and the heart function according to the present invention.

11 step of beating measurement
12 step of frontend signal removing
13 step of frequency domain transformation
14 step of energy spectrum transformation
15 step of normalization
151 step of energy normalization
152 step of frequency normalization
16 step of defining the heart index
17 step of computing the heart index
31 original signal
311 frontend beating signal
312 backend beating signal

DETAILED DESCRIPTION

A preferred embodiment of the present invention is described below to explain the features and the advantages of the claimed technology.

Please refer to FIG. 1, the preferred embodiment of the claimed analysis method about probing into relationship of beating signal and heart function includes: a step of beating measurement 11, a step of frontend signal removing 12, a step of frequency domain transformation 13, a step of energy spectrum transformation 14, a step of normalization 15, a step of defining the heart index 16 and a step of computing the heart index 17.

Figure 2:
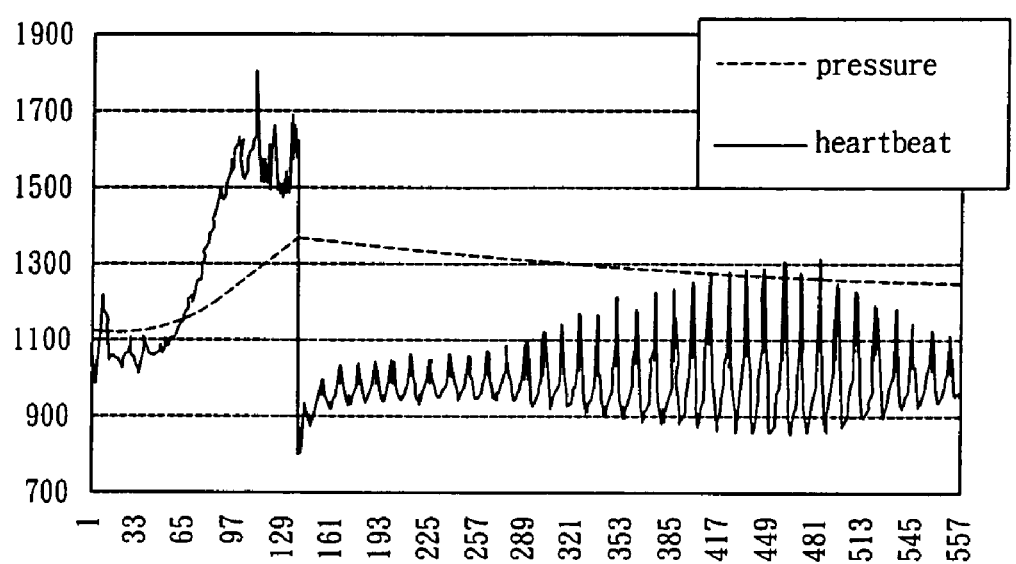
FIG. 2 is a complete original signal chart obtained by the step of beating measurement of the preferred embodiment.

In the step of beating measurement 11 of this embodiment, a electric manometer, which can detect 16 beating signal in one second, is used to measure the heartbeat of the subject. The measured original signal is shown in FIG. 2, and the dotted line means the pressure. The pressure belt of the manometer is pumped and the pressure is raised in the beginning, and the motor of the pump is stopped at the highest pressure and the pressure is gradually decreased. The filled line means the measured beating signal. The frontend beating signal 311 has more noise caused by the pump operation, and after the pump stopped, the backend beating signal is lowered and has regularity to analyze.

When the original time domain signal 31 transforms to the frequency domain, the beating signal spectrum diagram can help to understand and determine the signal feature and meaning. In this embodiment, the frontend beating signal 311 is proceeded with the step of frontend signal removing 12 (the reason id explained below), and the step of frequency domain transformation 13 is performed with the fast Fourier transform (FFT) calculation. The calculation is shown in [equation 1], and other conventional methods for transforming the time domain signal 31 to the frequency domain are also suitable.

$$X(n) = \sum_{k=0}^{N-1} x_0(k) W_N^{kn} \quad \text{[equation 1]}$$

wherein, $W_N = e^{-j\frac{2\pi}{N}}$ $x_0$: the original time domain signal
X: the spectrum of transforming the original signal to the frequency domain
N: the inputted signal count
$j: \sqrt{-1}$
n=0, 1, ... N−1

The length of the original signal $x_0$ is varied according to the pulse measuring time, and in this embodiment, using the signal detected 16 times/min. The sequence $x_0$ is performed a 1024 points FFT to obtain the spectrum X of transforming the original signal 31 to the frequency domain. After the step of frequency domain transformation 13, since the noise signal of the pump operation and the human beating signal are overlapped in the frequency domain, the step of frontend signal removing 12 should remove the frontend beating signal 311 before the pump stopped and perform the frequency domain transformation with the backend beating signal 312.

Figure 3A:
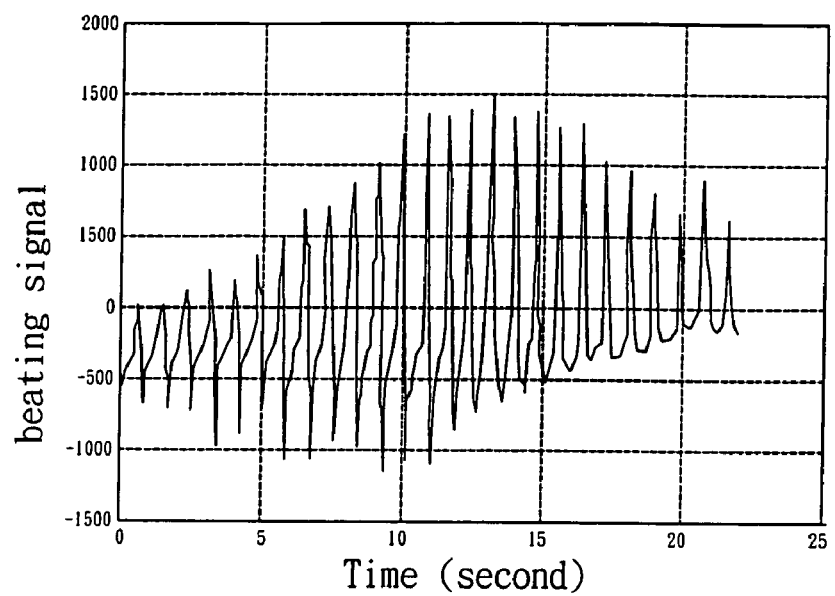
FIGS. 3a and 3b are a measured backend beating signal chart and an energy spectrum diagram of the backend beating signal after the energy spectrum transformation.
Figure 3B:
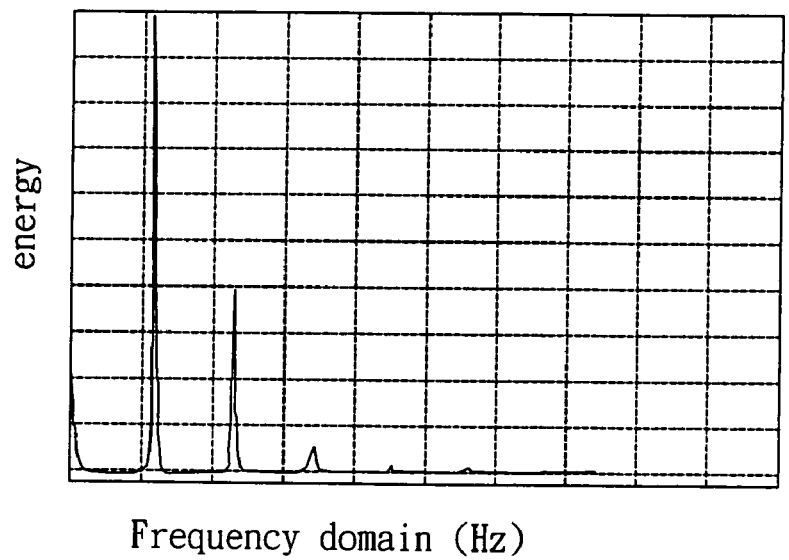

The step of energy spectrum transformation 14 is multiplying the spectrum X of the backend beating signal 312 obtained by the step of frequency domain transformation 13 with its conjugate value conj (X), and the power spectrum density S of X is obtained. The power spectrum density S means the energy distribution status of signals in the frequency domain, and can be shown by [equation 2]. FIGS. 3a and 3b show a measured backend beating signal 312 and an energy spectrum diagram of the backend beating signal 312 after transformation of steps 13 and 14.

$$S = X^* \text{conj}(X)/n \quad \text{[equation 2]}$$

Wherein, n: length of X

For evaluating whether the beating signal is affected by subject's status, a comparison research is made and found that although the heartbeat is faster, the energy is larger, and the blood pressure is varied after exercising, the signal features of the heart index are still obvious to be normalized and the subject doesn't need to rest a period of time. The present invention can be applied to subjects in any status without affecting the result.

In this embodiment, the step of normalization 15 includes a step of energy normalization 151 and a step of frequency normalization 152. The step of energy normalization 151 is selecting the amplitude of a maximum fundamental wave from the power spectrum density diagram in FIG. 3b, and the corresponding frequency is defined as the first main frequency which is generally located at 1 Hz (in the figure, the signal of 0 Hz shows the average value without zeroing and isn't related to vibration). The other waves with smaller amplitudes are called harmonic waves, and are defined as the second and third main frequencies. The amplitude of the first main frequency is defined 100% (the energy normalizing standard in this embodiment), and dividing the amplitudes of the harmonic waves with the amplitude of the first main frequency to clearly observe the amplitude proportion relationship of the energy after normalizing.

The step of frequency normalization 152 is defining the heartbeat 80 times/min, that is 1.33 time/sec, and an electric manometer which can detect 16 beating signals in one second is used to obtain 21.28 beating signals. The pulse count in one minute is divided with the normalizing standard 80 and is multiplied with the time sequence, and the beating status after frequency normalizing is obtained.

Figure 4A:
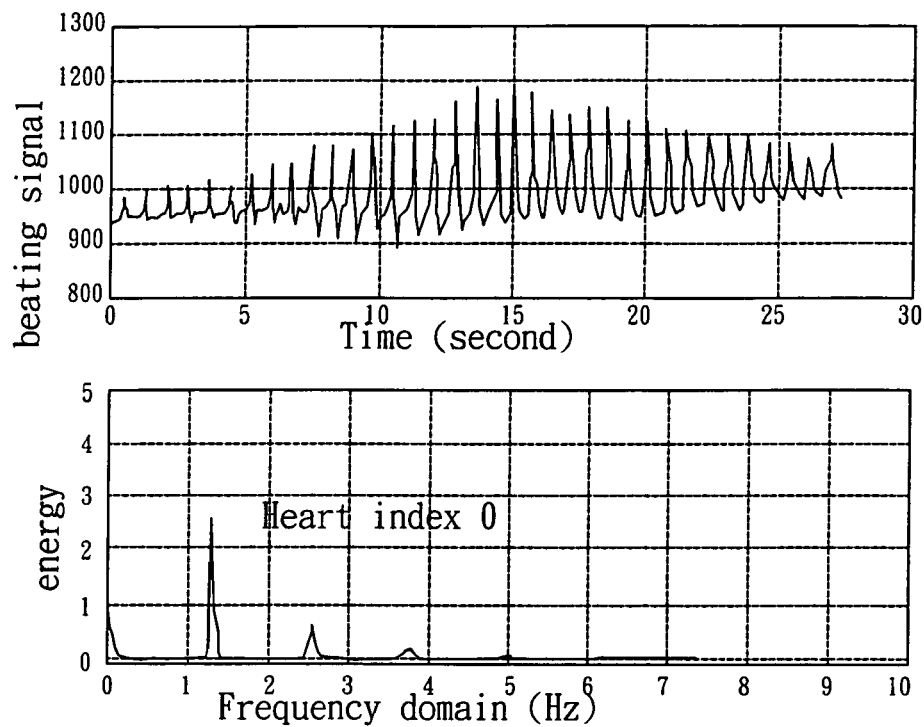
FIG. 4a is a backend beating signal and an energy spectrum diagram of a normal subject with heartbeat 80 times/min measured under rest status.
Figure 4B:
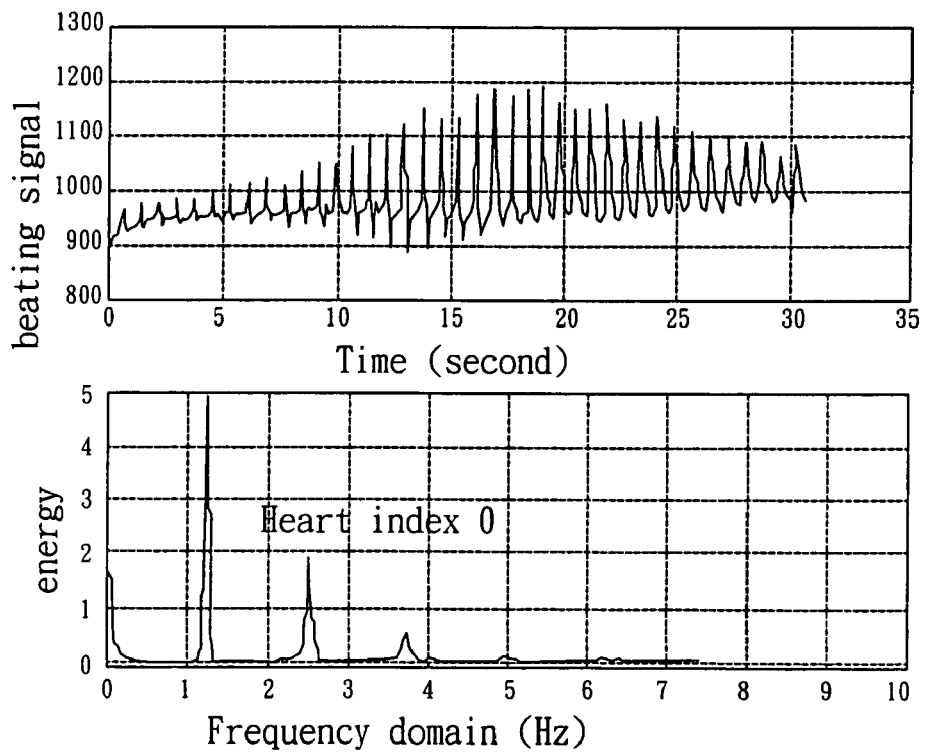
FIG. 4b is a result of the FIG. 4a after frequency normalization and energy normalization.

FIGS. 4 to 6 show the result of the step of normalization 15. FIG. 4a includes a backend beating signal 312 of a normal subject with heartbeat 80 times/min measured under rest status (the upper diagram) and an energy spectrum diagram of the backend beating signal 312 after normalizing with steps 13 and 14 (the lower diagram) The amplitude of the first main frequency shown in the energy spectrum diagram is about $2.8\times10^5$. FIG. 4b is a result of the FIG. 4a normalized the heartbeat as 80 times/min and the amplitude of the first main frequency as $5\times10^5$.

Figure 5A:
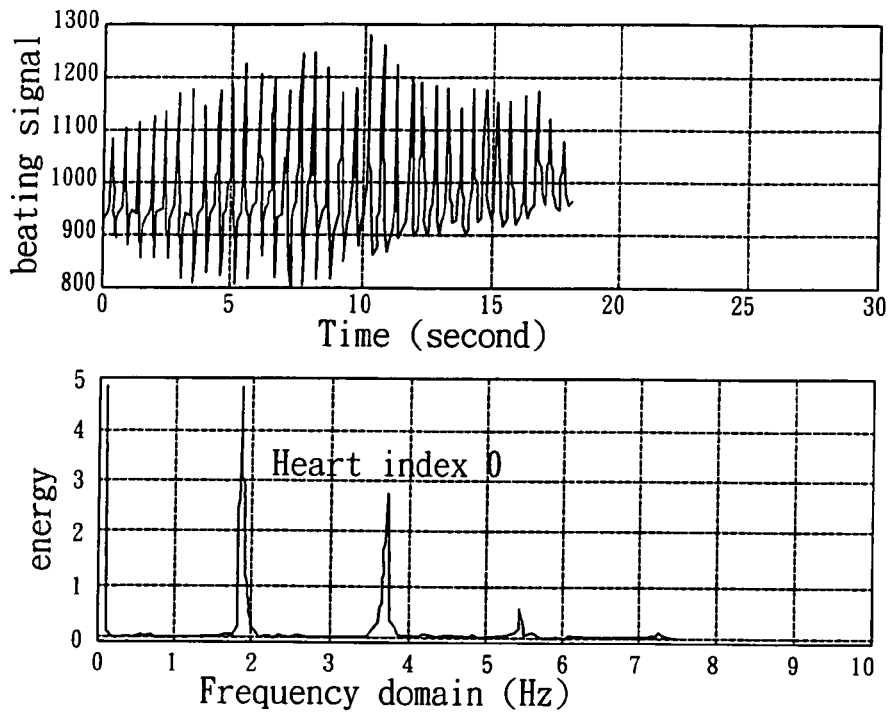
FIG. 5a is a backend beating signal and an energy spectrum diagram of a normal subject with heartbeat 120 times/min measured after exercising.
Figure 5B:
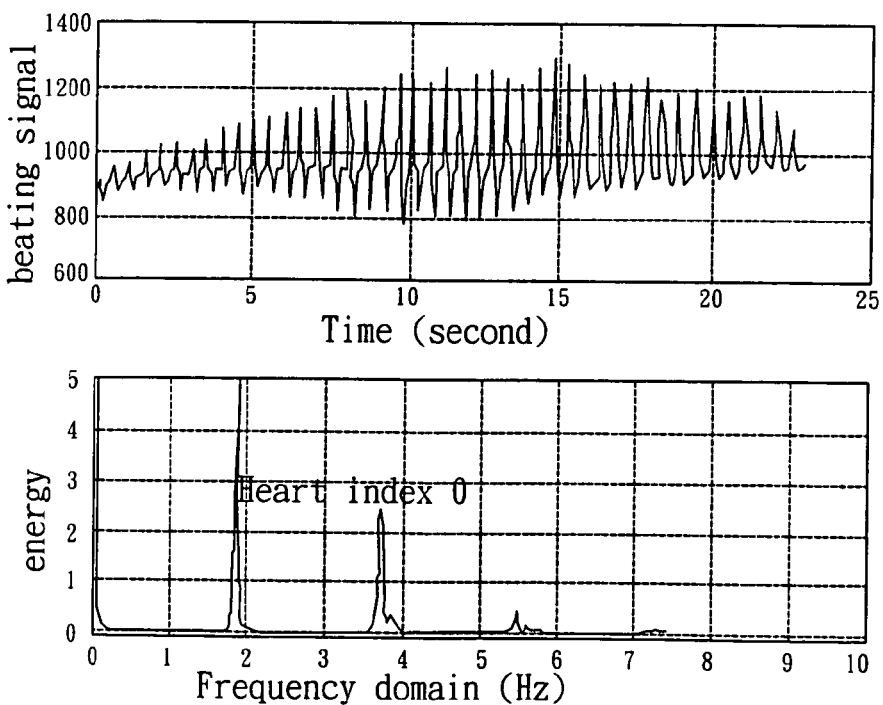
FIG. 5b is a result of the FIG. 5a after frequency normalization and energy normalization.

Similarly, FIG. 5a includes a backend beating signal 312 of the same subject with heartbeat 120 times/min measured after exercising (the upper diagram) and an energy spectrum diagram (the lower diagram). The amplitude of the first main frequency shown in the energy spectrum diagram is about $6.1\times10^5$. FIG. 5b is a result of the FIG. 5a normalized the heartbeat as 80 times/min and the amplitude of the first main frequency as $5\times10^5$.

Figure 6A:
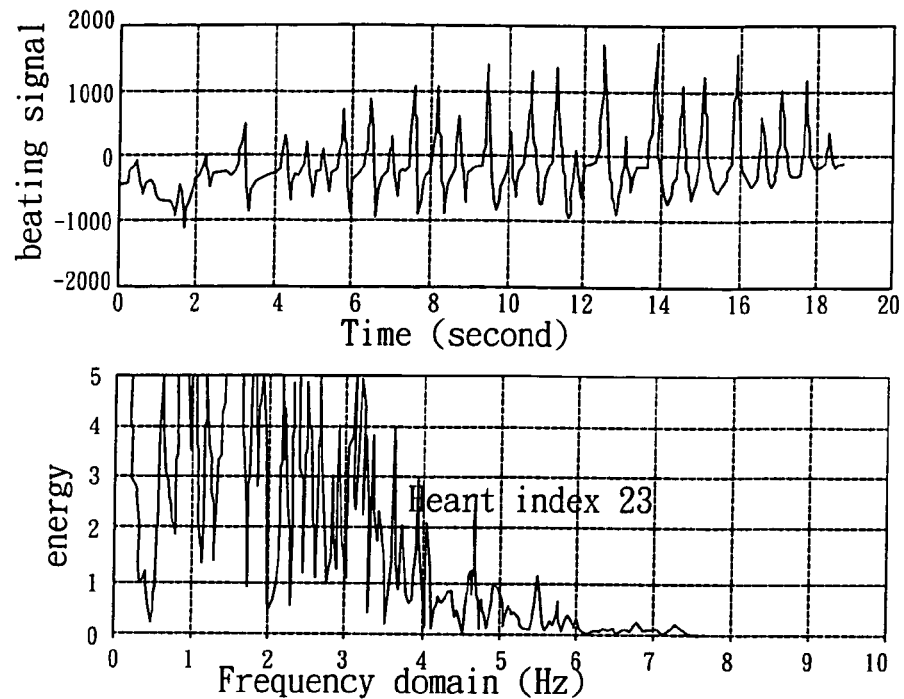
FIG. 6a is a backend beating signal and an energy spectrum diagram of a cardiomyopathy patient with heartbeat 65 times/min measured under rest status.
Figure 6B:
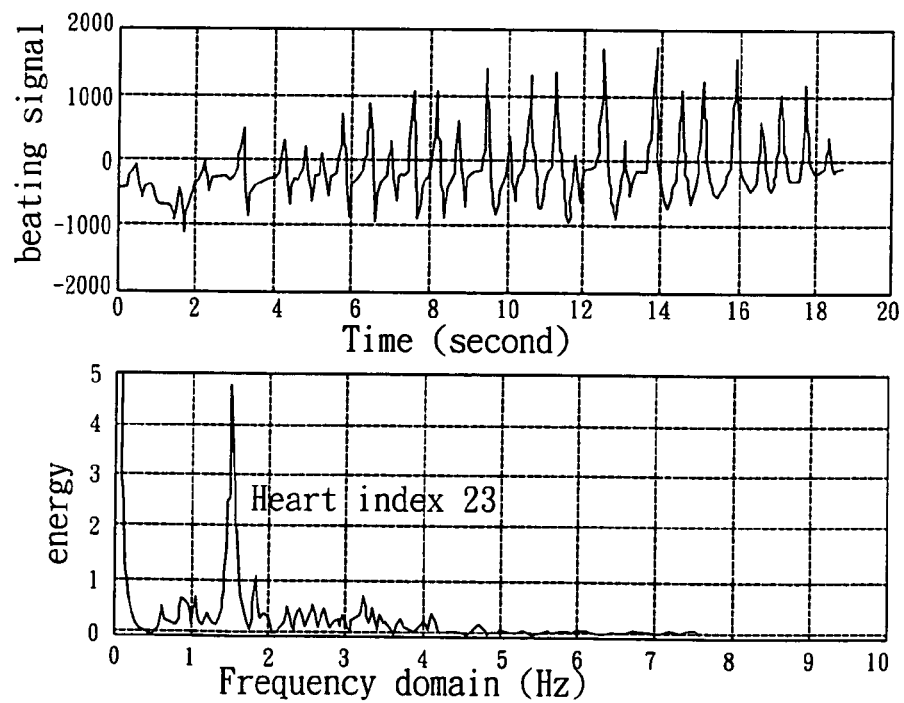
FIG. 6b is a result of the FIG. 6a after frequency normalization and energy normalization.

FIG. 6a includes a backend beating signal 312 (the upper diagram) and an energy spectrum diagram (the lower diagram) of a cardiomyopathy patient with heartbeat 65 times/min measured under rest status. The amplitude of the first main frequency shown in the energy spectrum diagram is about $8.9\times10^5$. FIG. 6b is a result of the FIG. 6a normalized the heartbeat as 80 times/min and the amplitude of the first main frequency as $5\times10^5$. In FIG. 6b, the main frequency position of the cardiomyopathy patient is more difficult to identify than that of a normal person, and the non-zero energy spectrums between each main frequencies are frequently appeared.

After analyzing a large number of measured data, the beating energy spectrum diagram of a non-heart disease person can be read out 4 to 5 main energy distributions (the main frequencies) according to the personal heartbeat speed. The biggest energy is found near 1 Hz, and the energy decreases gradually forward to the high frequency end. Besides the 4 or 5 main spectrums, no other obvious spectrum distribution is found and the value on the frequency axis is generally zero.

The beating energy spectrum diagram of a heart disease patient can be also read out 4 to 5 main frequencies, but some spectrums whose energy is smaller than that of the main frequency are observed. Wider the non-zero spectrum distributing means more irregular the captured beating signal is, and includes unstable signals. Moreover, the worse one has much larger irregular signal energy and cannot determine position of the main frequency. So, in the energy spectrum diagram of a patient, besides the main frequencies, the amount of the non-zero energies appeared on the frequency domain is greatly related to whether the patient has a heart disease.

With the step of defining the heart index 16 and the step of computing the heart index 17, the determining criteria of the relationship between the beating signal energy spectrum analysis and the heart function can be quantified and formulated. The claimed invention can be performed in a software program operated with a storage media storing the software program (such as the floppy disk, the optical disk or the hard disk) and an electric device that can execute this software program (such as the computer, the PDA or the clinical equipment) to rapidly compute and provide the subject for reference.

Figure 7:
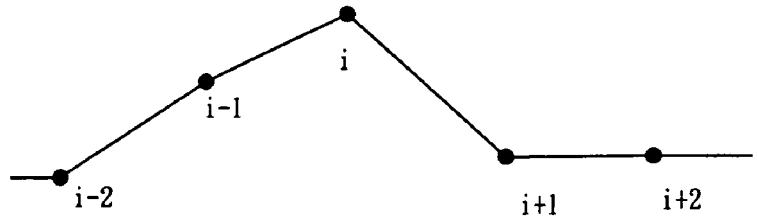
FIG. 7 is a schematic diagram of defining steps of a heart index according to the preferred embodiment.

In the step of defining the heart index 16, the heart index is defined as follows. Firstly, in the energy spectrum diagram obtained by the step 15, defining the 0 point to the first main frequency as the first interval, the first to second main frequencies as the second interval, the second to third main frequencies as the third interval, and the third to fourth even fifth main frequencies as the fourth interval. As shown in FIG. 7, when the energy spectrum distribution status of the intervals matches [equation 3], a meaningful spike at i point is defined.

if $[S(i)-S(i-1)>V_0$ or $S(i)-S(i-2)>V_0]$ and $[S(i)-S(i+1)>V_0$ or $S(i)-S(i+2)>V_0]$ [equation 3]

Wherein, $V_0=P_1/50$, $P_1$ is the amplitude of the first main frequency. The heart index is defined as a sum of the meaningful spike counts in the first to fourth intervals.

In the step of computing the heart index 17, the definition of step 16 is used to compute the heart indexes of FIGS. 4b, 5b and 6b, and the heart indexes of FIGS. 4b and 5b are all 0. In other words, although the normalized heartbeat and spectrum energy values of same subject before and after exercising are different, the heart indexes are the same and not affected by status of the subject. In FIG. 6b, the heart index of a heart disease patient is 23 after normalizing, and is different to that in FIGS. 4b and 5b, so the heart index can be a quantified and objective determining criteria to determine the heart disease.

Please pay attention to that the heart index is not limited by [equation 3], and the parameter $V_0$ can be also adjusted. The computing methods utilizing the variation of the strike or other waves in the energy spectrum diagram to compute the heart index are all claimed in the present invention.

The clinical observation and analysis result in one hospital is disclosed below. The 201 subjects are diagnosed in the department of cardiac medical, wherein the amount of the diagnosed heart disease patients is 53 and the amount of the non-heart disease patients is 148. With the heart index computing and the clinical diagnosis, the heart index can be divided as follows to be the reference for determining the heart function:

The heart index above 7: the abnormal beating frequency of heart is frequent and obvious, and the cardiac muscle systole is abnormal, and this is the feature of multiple heart diseases;

The heart index 4~6: The heart beats abnormal, and this is the feature of the highly dangerous group of the heart disease or already got a heart disease; and The heart index below 3: The heart beating frequency is normal, and the heart index of a healthy person is generally 0.

If analyzing the 53 diagnosed heart disease patients, wherein amount of the valvular heart disease patient is 13, amount of the cardiomyopathy patient (includes the cardiomyopathy and myocarditis) is 12, amount of the arrhythmia patient is 7, and amount of the coronary artery patient is 21. The related statistics of the diseases and the heart index is shown in Table 1.

TABLE 1

Related statistics of diseases and heart index

| Diseases | Heart index | | |
|---|---|---|---|
| | 0~3 (Percentage) | 4~6 (Percentage) | Above 7 (Percentage) |
| valvular heart disease | 1 (7.69%) | 1 (7.69%) | 11 (84.62%) |
| | | 12 (92.31%) | |
| cardiomyopathy disease | 1 (8.33%) | 3 (25.00%) | 8 (66.67%) |
| | | 11 (91.67%) | |
| Arrhythmia disease | 1 (14.29%) | 4 (57.14%) | 2 (28.57%) |
| | | 6 (85.71%) | |
| coronary artery disease | 7 (33.33%) | 6 (28.57%) | 8 (38.10%) |
| | | 14 (66.67%) | |
| sum | 10* (18.87%) | 14 (26.42%) | 29 (54.72%) |
| | | 43 (81.13%) | |

In Table 1, between all samples, the valvular heart disease is 13. The abnormal status detecting rate is 84.62% and the suspected abnormal status detecting rate is 7.69%, so the total detecting rate is 92.31%. Between the 11 cardiomyopathy disease samples, the abnormal status detecting rate is 66.67% and the suspected abnormal status detecting rate is 25%, so the total detecting rate is 91.67%. Between the 7 arrhythmia disease samples, the abnormal status detecting rate is 28.57% and the suspected abnormal status detecting rate is 57.14%, so the total detecting rate is 85.71%. Between the 21 coronary artery disease samples, the abnormal status detecting rate is 38.10% and the suspected abnormal status detecting rate is 28.57%, so the total detecting rate is 66.67% and the missed rate is 33.33% which will be explained below.

The amount of total samples is only 53. Since the body is too small, the percentage is only for reference and cannot be a conclusion.

The relationship and possible cause of the heart diseases and the heart indexes are described below:

Firstly, the valvular heart disease can be sorted into the aortic valve abnormality, the mitral valve abnormality, the pulmonary valve abnormality, the tricuspid valve abnormality, and the atrium or ventricle septal defect. Different reasons will lead to different beating spectrum distribution. For example, if the aortic valve is fibered by the congenital defect or calcification and narrowed the aortic valve, the narrowed aortic valve will block the blood of left ventricle into the aortic while the heart systole, and the narrowed degree will lead to different consequences. At this moment, the heart will try to compensate the imbalance situation of the blood circulation (the compensation effect), and prevent the blood flowed from the left ventricle to the aorta few. There are some emergency measures of the heart:

1. strengthening the systolic power of the left ventricle, and this will cause the left ventricular hypertrophy to push the blood; and
2. extending the systole time, and more blood will flow from the left ventricle into the aorta when the systole time is extended.

Figure 8:
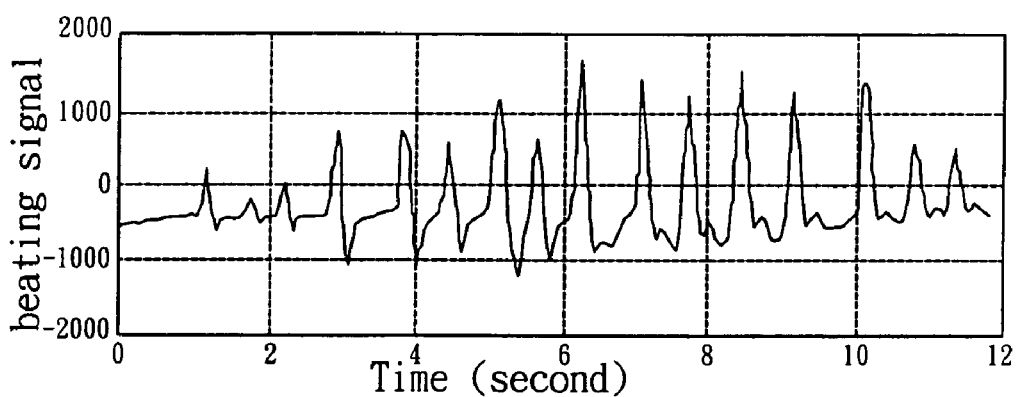
FIG. 8 is a captured signal and an energy spectrum analysis diagram of a valvular heart disease patient's heartbeat.
Figure 8:
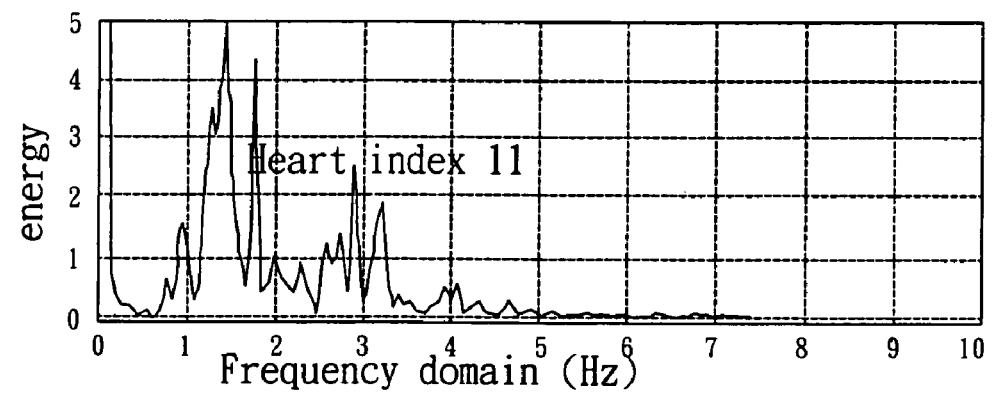

The above-mentioned methods will increase workload and strengthen blood pressure of the left ventricle. The heart works powerfully and rapidly, but the pulse is still weak and the patient feels tired, hard breathed, dizzy or chest pain. As show in FIG. 8, which shows a captured signal and an energy spectrum analysis diagram of a valvular heart disease patient's heartbeat. In the energy spectrum diagram, when flowing from the left ventricle into the aorta, the blood is blocked and has an extra abnormal signal. In addition, when the systole time is increased or the power is changed, the analysis can also show the difference, and the heart index is 22.

Figure 9:
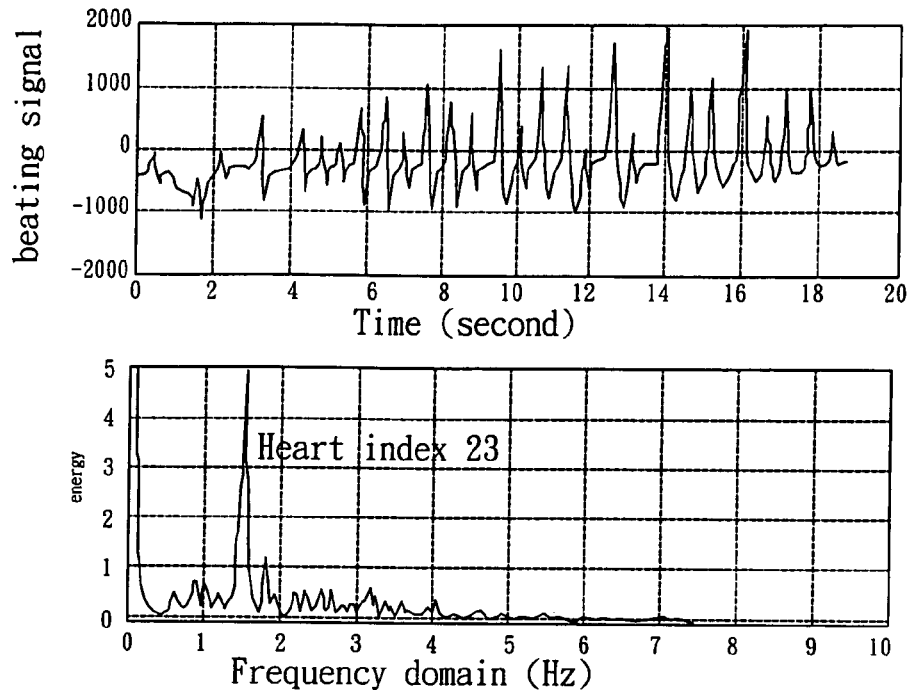
FIG. 9 is a captured signal and an energy spectrum analysis diagram of a cardiomyopathy patient's heartbeat.

FIG. 9 is a captured signal and an energy spectrum analysis diagram of a cardiomyopathy patient's heartbeat, and the heart index is 22.

Figure 10:
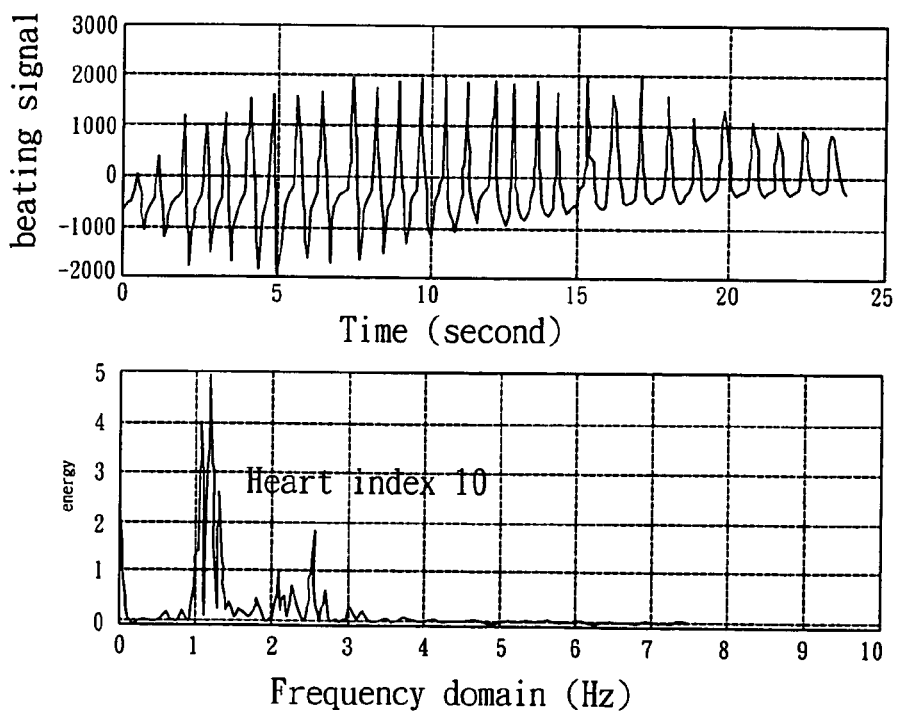
FIG. 10 is a captured signal and an energy spectrum analysis diagram of an arrhythmia patient's heartbeat.

FIG. 10 is a captured signal and an energy spectrum analysis diagram of an arrhythmia patient's heartbeat, and the heart index is 5. In the diagrams of the arrhythmia patients, the heart indexes are generally 4 to 6 with percentage 57%, and the heart index greater than 7 is 28.57%. Although the arrhythmia can be detected with the claimed method, the energy spectrum diagram has only few extra frequency distributions, and unlike that of the valvular heart disease or cardiomyopathy patients having obvious features with above 10 or 20 heart index. In the diagrams of the arrhythmia patients, although the missing percentage is 14.29%, the value has no statistics meaning with few samples. The missing case is a 75 years old man, whose signal is particularly weak and cannot find the abnormality.

Figure 11:
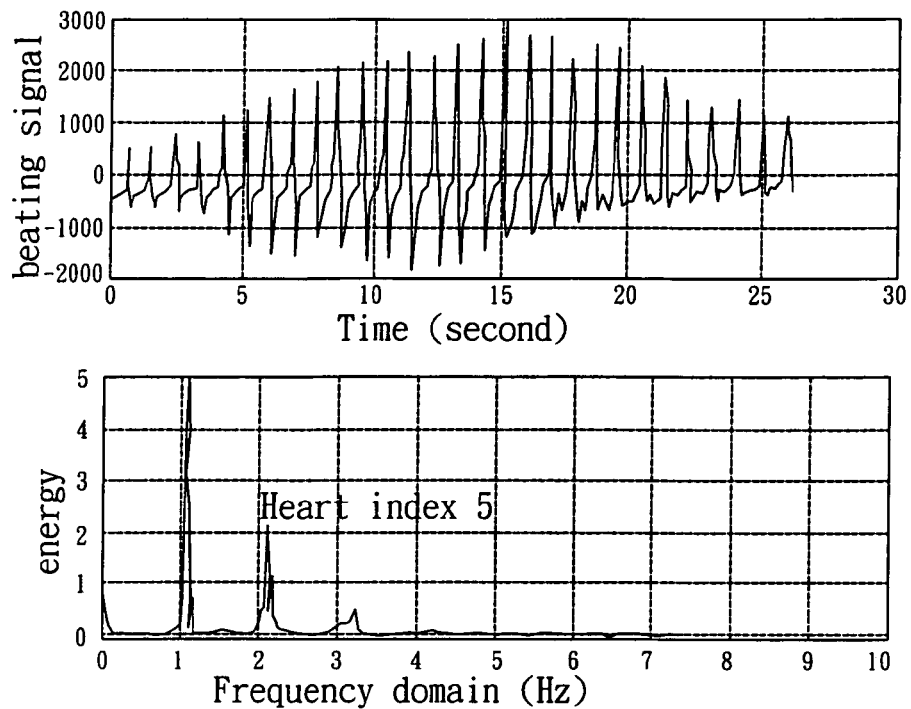
FIG. 11 is a captured signal and an energy spectrum analysis diagram of a coronary artery patient's heartbeat.

FIG. 11 is a captured signal and an energy spectrum analysis diagram of a coronary artery patient's heartbeat, and the heart index is 5. The block in the coronary artery is generally caused by the atherosclerosis. The cholesterol and lipoids are coated inside the artery, and the coronary artery diseases also include the congenital defect or the coronary artery abnormally dilation. When the coronary artery has pathological changes and cannot supply heart muscle oxygen and nutrition, the ischemic heart disease is happened. The ischemic heart disease cannot be observed while resting, but when the workload of heart is increased (such as exercising, weather changed or the mood emoted), the patient will have angina pectoris for lacking oxygen.

In cases of the coronary artery disease, the detecting percentage is 38.1%, the suspected abnormal percentage is 28.57%, and the missing percentage is 33.33%. This result means that during the coronary artery patients, about 60% will have the abnormal systole frequency of the heart muscle, and above 30% cannot be found while resting.

Among the above-mentioned 148 non-heart disease subjects, the hypertension patients is the most with 110 cases, and the related statistics of the heart index of the hypertension and non-hypertension patients is shown in Table 2.

TABLE 2

Related statistics of the heart index of the hypertension and non-hypertension patients

| Diseases | Heart index | | |
|---|---|---|---|
| | 0~3 (percentage) | 4~6 (percentage) | Above 7 (percentage) |
| hypertension | 70 (63.64%) | 26 (23.64%) | 14 (12.73%) |
| | | 40 (36.36%) | |
| non-hypertension non-heart disease | 31 (81.58%) | 5 (13.16%) | 2 (5.26%) |
| | | 7 (18.42%) | |
| sum | 101 (68.24%) | 31 (20.95%) | 16 (10.81%) |
| | | 47 (31.76%)** | |

Figure 12:
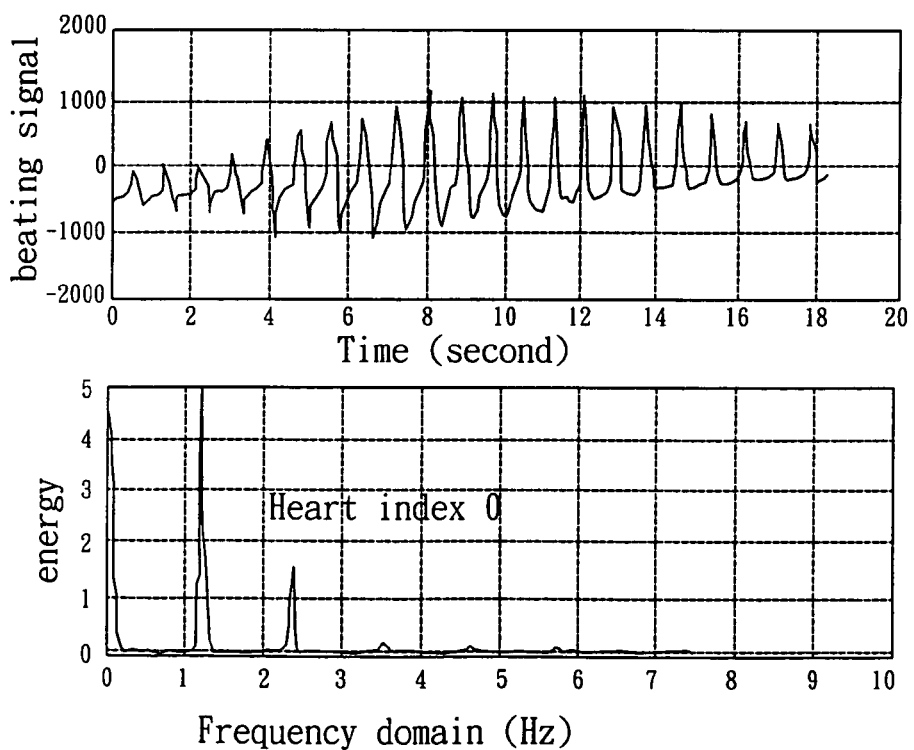
FIG. 12 is a captured signal and an energy spectrum analysis diagram of a non-heart disease patient's heartbeat.

In Table 2, the percentage of the hypertension group whose heart index greater than 4 is 36.37%, that is higher than that of the non-hypertension group, 18.42%. In other words, the abnormal or suspected abnormal percentage of the myocardium systole frequency of the hypertension patient is high than that of the normal people. In fact, the hypertension group is the highly dangerous group of getting the heart disease, and some of them already have the symptom. FIG. 12 is a captured signal and an energy spectrum analysis diagram of a non-heart disease patient's heartbeat, and the heart index is 0. The frequency distribution is regularly and clearly different from that of FIGS. 8 to 11.

In contrast to the prior art, the present invention has these advantages:

1. The present invention only utilizes the electric manometer to measure the beating signal and be the reference of the heart function without other extra or expansive detecting equipments, so the claimed method is a cheap, safe, simple and popular one that can be popularized to every families. The users can determine the heart function when measuring the blood pressure to be the reference of health care.
2. With the difference of the beating energy spectrum diagram between FIGS. 4a, 5a and 6a, position of the main frequencies of the cardiomyopathy patient is difficult to identify than that of a normal person. The non-zero energy spectrum is frequently appeared between each main frequency, so the beating energy spectrum diagram can be a reference to determine whether the subject has a heart disease.
3. With normalizing the energy spectrum, features of the heart index are all similar under resting or exercising status. The present invention can be used under any status, time or place, and has much flexibility than other detecting methods.
4. As described above, the present invention utilizes a software program and a computer to rapidly compute. The subject can immediately get the result and can prevent as soon as possible, and the doctor can also take a suitable treat as soon as possible.
5. In the actual application, the detected percentage of the heart disease with the present invention depends on kinds of the heart diseases, and not every kind of heart disease can lead to the myocardium systole or beating frequency abnormality. The average detected percentage of the mentioned samples is about 80%, and can prove the practicability and reliability.

6. In the mentioned samples, people diagnosed as normal by the doctor still have about 32% suspected (especially the hypertension patients) so the detecting standard of the heart disease of the present invention is strict than that of doctors, and can warn the patients in advance.

Those skilled in the art will readily observe that numerous modifications and alterations of the device may be made while retaining the teachings of the invention. Accordingly, the above disclosure should be construed as limited only by the metes and bounds of the appended claims.

What is claimed is:

1. An analysis method using a relationship between a beating signal and a heart function, the beating signal being measured from a subject under any activity condition in a period of time with an electric manometer, the method comprising the steps of:
   (a) transforming the beating signal into a power spectrum by performing a power spectrum transformation;
   (b) normalizing the power spectrum output by the power spectrum transformation; and
   (c) computing a pre-defined heart index from the normalized power spectrum.

2. The method of claim 1, wherein the step of transforming the beating signal is preceded by the step of omitting the beating signal in a time period before a pump of the electric manometer has stopped.

3. The method of claim 1, wherein the step of transforming the beating signal comprises:
   performing a frequency domain transformation of the beating signal to obtain a corresponding spectrum; and
   computing a power spectrum density of the spectrum.

4. The method of claim 3, wherein the step of performing a frequency domain transformation is performed with a fast Fourier transform (FFT).

5. The method of claim 1, wherein the step of normalizing the power spectrum comprises an energy normalization step and a frequency normalization step.

6. The method of claim 5, wherein the energy normalization step utilizes amplitude of a maximum fundamental wave in the power spectrum to be a normalizing standard.

7. The method of claim 5, wherein the frequency normalization step utilizes a selected heartbeat to be a normalizing standard.

8. The method of claim 1, wherein the step of computing a pre-defined heart index is preceded by the step of defining the heart index, the heart index being defined as a sum of a meaningful spike count in all intervals of a normalized energy spectrum diagram.

9. The method of claim 8, wherein the meaningful spike is defined by:

if $[S(i)-S(i-1)>V_0$ or $S(i)-S(i-2)>V_0]$ and $[S(i)-S(i+1)>V_0$ or $S(i)-S(i+2)>V_0]$ the $i_{th}$ point is the meaningful spike, wherein S(i) is the normalized energy
   spectrum of the $i_{th}$ point, $V_0=P_1/N$, P1 is the amplitude of the maximum fundamental wave in the normalized energy spectrum, and N is a constant.

10. The method of claim 9, wherein the constant N is 50.

11. A storage media storing a program that can execute the method of claim 1.

12. An analysis method using a relationship between a beating signal and a heart function, the beating signal being measured from a subject under any activity condition in a period of time with an electric manometer, the method comprising the steps of:
   (a) omitting the beating signal in a time period before a pump of the electric manometer has stopped;
   (b) performing a frequency domain transformation of the beating signal to obtain a corresponding spectrum; and
   (c) computing a power spectrum density of the spectrum to obtain a corresponding energy spectrum diagram.

13. The method of claim 12, wherein the step of computing a power spectrum density is preceded by the step of normalizing the energy spectrum diagram.

14. The method of claim 13, further comprising a step of computing a pre-defined heart index using the normalized energy spectrum diagram.

15. A storage media storing a program that can execute the method of claim 12.

16. A method for determining a heart function from a beating signal, the beating signal being measured from a subject under any activity condition in a period of time with an electric manometer, the method comprising the steps of:
   (a) transforming the beating signal into a power spectrum by performing a power spectrum transformation;
   (b) normalizing the power spectrum output by the power spectrum transformation;
   (c) computing a pre-defined heart index from the normalized power spectrum; and
   (d) determining the heart function of the subject according to the heart index.

17. The method of claim 16, wherein the step of determining the heart function of the subject includes the step of determining whether the subject has a heart disease.

18. The method of claim 16 or claim 17, wherein the step of determining the heart function of the subject includes the step of determining a type of heart disease of the subject.

19. A storage media storing a program that can execute the method of claim 16.

* * * * *